US00PP29392P3

(12) United States Plant Patent
van Rijn

(10) Patent No.: US PP29,392 P3
(45) Date of Patent: Jun. 12, 2018

(54) *ANTHURIUM* PLANT NAMED 'ARAANTRED1'

(50) Latin Name: *Anthurium andraeanum*
Varietal Denomination: ARAANTRED1

(71) Applicant: J&D Horticulture B.V., De Lier (NL)

(72) Inventor: Silvia van Rijn, De Lier (NL)

(73) Assignee: J&D Horticulture B.V., De Lier (NL)

( * ) Notice: Subject to any disclaimer, the term of this patent is extended or adjusted under 35 U.S.C. 154(b) by 0 days. days.

(21) Appl. No.: 15/530,809

(22) Filed: Mar. 3, 2017

(65) Prior Publication Data

US 2017/0265367 P1 Sep. 14, 2017

(30) Foreign Application Priority Data

Mar. 10, 2016 (QZ) ..... PBR 2016/0699

(51) Int. Cl.
*A01H 5/02* (2018.01)

(52) U.S. Cl.
USPC ..... Plt./365

(58) Field of Classification Search
USPC ..... Plt./365, 369
CPC ..... A01H 5/02; A01H 5/00; A01H 5/12
See application file for complete search history.

*Primary Examiner* — June Hwu
(74) *Attorney, Agent, or Firm* — Samuel R. McCoy, Jr.

(57) ABSTRACT

'ARAANTRED1' is a new and distinctive variety of *Anthurium* which is characterized by the combination of a vibrant red, glossy spathe with a nearly horizontal aspect and a relatively short spadix which is colored white with a yellow apex, an abundance of narrowly cordate foliage which is dark green and glossy, inflorescences held above the foliage, and the stability of all characteristics from generation to generation. The new variety is typically produced as an indoor ornamental plant.

3 Drawing Sheets

Latin name of the genus and species: The Latin name of the genus and species of the novel variety disclosed herein is *Anthurium andraeanum* Linden ex Andre.

Variety denomination: The inventive variety of *Anthurium* disclosed herein has been given the variety denomination 'ARAANTRED1'.

CROSS REFERENCE TO RELATED APPLICATIONS

This application claims priority to the Community Plant Variety Rights application number 2016/0699, filed Mar. 10, 2016, which is herein incorporated by reference.

BACKGROUND OF THE INVENTION

Parentage: The new cultivar is a seedling selection which resulted from the controlled pollination of *Anthurium andraeanum* 'K37', the seed parent, and *Anthurium andraeanum* 'K38', the pollen parent. Both parents are developed and owned by the inventor and were never commercially released. Said cross was performed by the inventor in De Lier, The Netherlands, in June of 2013. Seeds were harvested from 'K38', sown, and grown to maturity in order to evaluate for unique characteristics which may be of commercial value. In September of 2014, after evaluating the seedlings for approximately one and a half years, one progeny was observed to exhibit good plant vigor with a unique combination of vibrant red, glossy spathes and an abundance of attractive narrowly-cordate foliage. In December of 2014, after further evaluation to confirm the unique characteristics, the new cultivar was selected for commercialization and given the breeder denomination 'ARAANTRED1'.

Asexual Reproduction: Asexual reproduction of 'ARAANTRED1', by way of meristematic tissue culture, was first performed in December of 2014 at a laboratory in De Lier, the Netherlands. Four successive generations so produced have shown that the unique features of the instant cultivar are stable and reproduced true to type.

SUMMARY OF THE INVENTION

The cultivar 'ARAANTRED1' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anthurium* cultivar 'ARAANTRED1'. These traits, in combination, distinguish 'ARAANTRED1' as a new and distinct cultivar.

1. *Anthurium* 'ARAANTRED1' is a robust, moderately vigor herbaceous perennial with a broad, upright growth habit; and
2. *Anthurium* 'ARAANTRED1' exhibits an abundance of relatively small narrowly-cordate leaves which are dark green and glossy; and
3. *Anthurium* 'ARAANTRED1' exhibits inflorescences held above the foliage; and
4. *Anthurium* 'ARAANTRED1' exhibits an inflorescence comprised of a vibrant red, glossy spathe and a relatively short spadix with a rounded apex; and
5. *Anthurium* 'ARAANTRED1' exhibits a spathe that maintains its vibrant red color for a relatively long period of time before fading.

Figure 1:
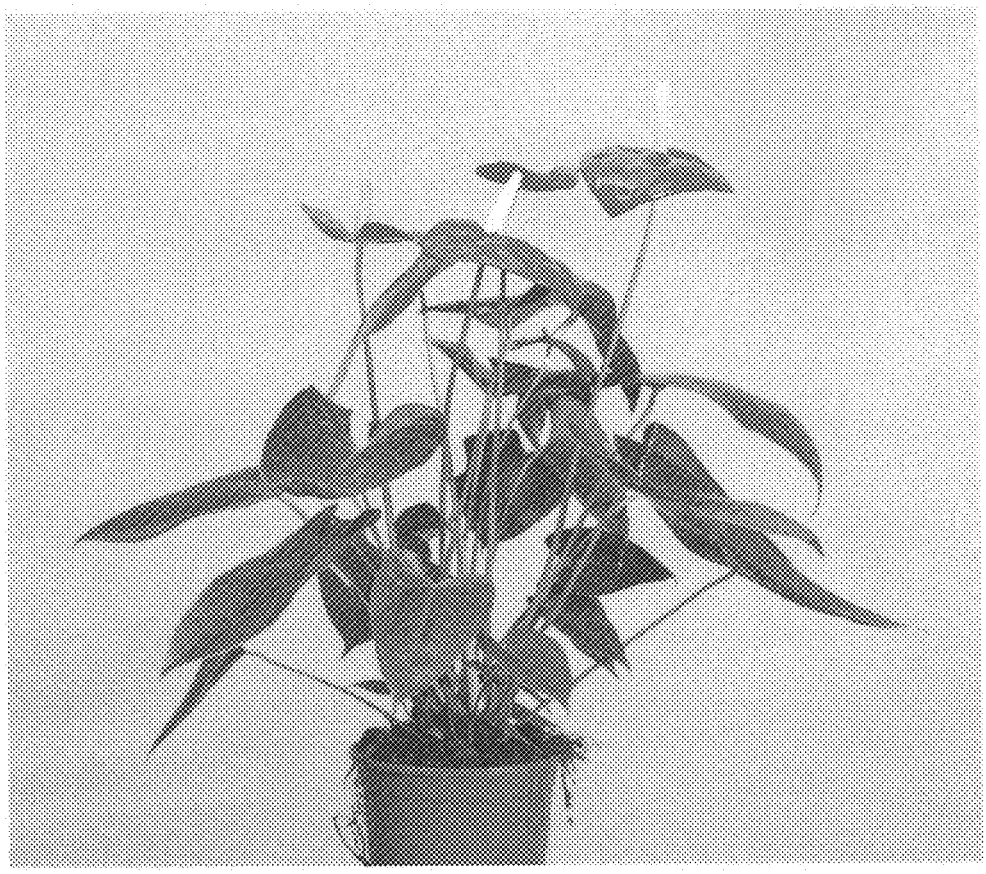
FIG. 1 shows, as nearly true as it is reasonably possible to make the same in color illustrations of this type, an exemplary plant of 'ARAANTRED1', grown in a greenhouse in De Lier, the Netherlands. The plant shown is approximately 1 year old from a rooted cutting, potted into a 14 cm nursery pot.
Figure 2:
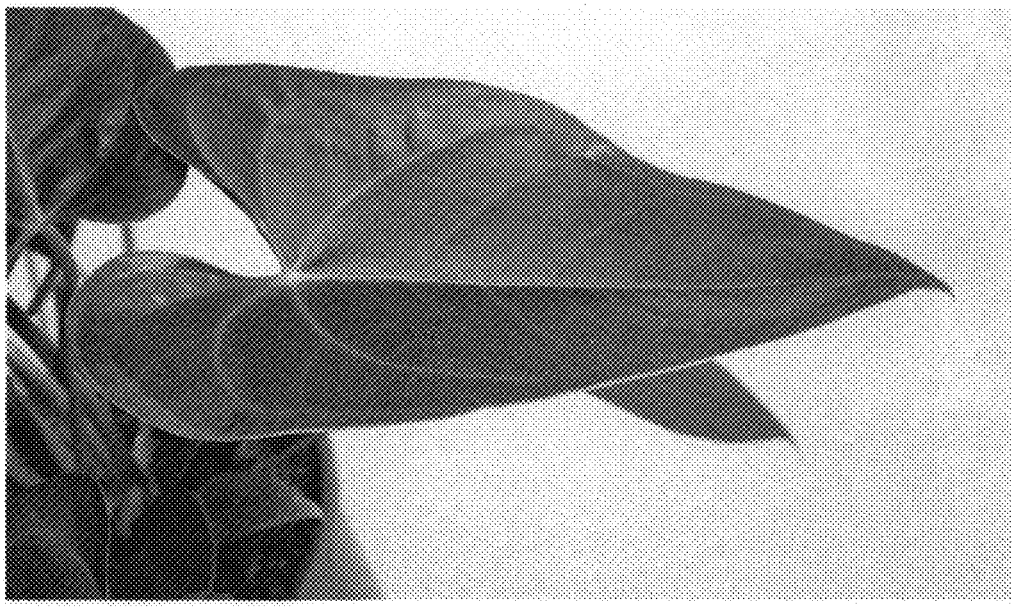
FIG. 2 shows, as nearly true as it is reasonably possible to make the same in color illustrations of this type, the typical foliage of 'ARAANTRED1'.
Figure 3:
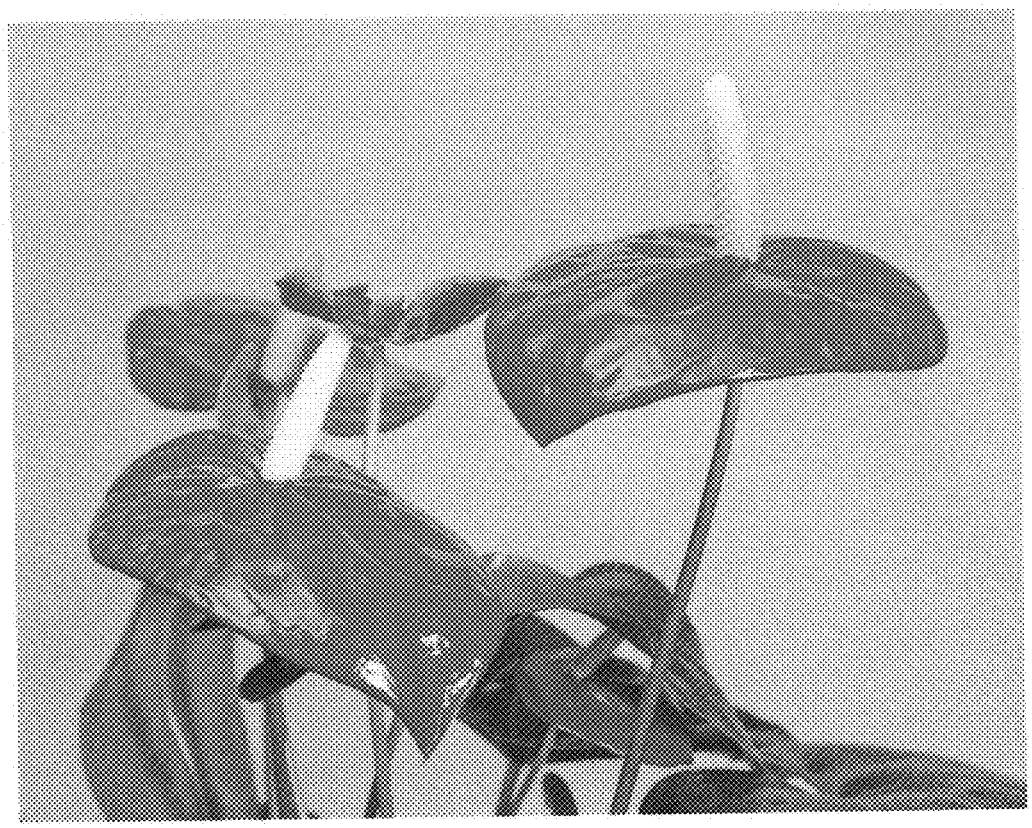
FIG. 3 shows, as nearly true as it is reasonably possible to make the same in color illustrations of this type, the typical inflorescence of 'ARAANTRED1'.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Anthurium* known as 'ARAANTRED1', based upon observations made from a sample set of plants grown in 9 cm nursery pots which were approximately one year old from a rooted cutting. Plants were grown in a greenhouse in De Lier, The Netherlands, utilizing conventional greenhouse production protocols for *Anthurium*, which consisted of regular irrigation by way of ebb and flood watering benches and fertilizer applications of a complete fertilizer with micro nutrients at an EC value ranging from 1.0 to 1.8. No chemical pest or disease measures were utilized in production. Young plants are assimilated to the greenhouse under shade cloth and later move to light levels ranging from 3000 to 4000 lux for the final 5 months of production. Observation data was recorded in February of 2017.

Those skilled in the art will appreciate that certain characteristics will vary with older or, conversely, with younger plants. 'ARAANTRED1' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, sixth edition.

A botanical description of 'ARAANTRED1' and comparisons with the parents and the most similar variety of common knowledge are provided below.

General plant description:

*Growth rate.*—Moderately fast.

*Plant vigor.*—Moderately vigorous.

*Growth habit.*—Clump-forming herbaceous perennial; broad upright.

*Plant shape.*—Broad obovate to globular with flowers sitting above the foliage.

*Height.*—35.5 cm in height, to the highest leaf; 43.5 cm to top of highest flower.

*Width.*—Average 49.3 cm in width.

*Propagation.*—Stem cuttings and meristematic tissue culture.

*Time to initiate roots.*—Approximately 30 days to initiate roots at approximately 23 degrees Centigrade.

*Time to produce a finished marketable plant.*—Approximately 30 to 35 weeks to produce a marketable plant in a 14 cm nursery pot.

*Environmental tolerances.*—Adapt to, at least, USDA Zones 10 to 13 and temperatures ranging from as high as 40 degrees Celsius and as low as 5 degrees Celsius; moderate to high tolerance to rain; low tolerance to wind.

*Pest resistance and susceptibility.*—Plants have not been observed to be susceptible or resistant to pathogens and pests common to *Anthurium*.

Root system:

*Root structure; texture.*—Not very dense; non-fibrous; moderately fleshy.

*Dimensions.*—Average length of 15.0 cm long and 0.3 cm in diameter.

*Color.*—Yellow-white, nearest to a combination of RHS 158A and 158B.

Stems:

*Branching characteristics.*—Basally-branched plant with leaves growing in small clumps which form short lateral branches.

*Quantity of clumps per plant.*—3.

*Quantity of additional clumps per year.*—3.

*Lateral branches.*—Dimensions — 2.0 cm long and 0.8 cm in diameter. Aspect — Approximately 10 degrees from vertical. Cross-section — Round. Texture and luster — Smooth, glabrous, and moderately glossy. Strength — Strong. Color, juvenile — Yellow-green, nearest to RHS 150D. Color, mature — Yellow-green, nearest to RHS 150D. Color at internodes — Yellow-green, nearest to RHS 150D.

Foliage:

*Arrangement.*—Alternate.

*Division.*—Simple.

*Quantity of leaves per lateral branch.*—7 leaves per clump.

*Quantity of shoots per plant.*—Average of 8.

*Leaf shape.*—Narrowly cordate.

*Leaf apex.*—Apiculate.

*Leaf base.*—Deeply cordate; lobes free.

*Aspect.*—Slightly concave.

*Leaf length.*—Average 19.2 cm in length.

*Leaf width.*—Average 10.6 cm in width.

*Leaf margin.*—Entire; very slightly undulate.

*Texture and luster, adaxial surface.*—Smooth, glabrous and glossy.

*Texture and luster, abaxial surface.*—Smooth, glabrous and glossy.

*Juvenile color, adaxial surface.*—In between green, nearest to RHS 143A, and yellow-green, RHS 144A, yet darker.

*Juvenile color, abaxial surface.*—Yellow-green, nearest to RHS 146B.

*Mature color, adaxial surface.*—Nearest to a combination of green, RHS NN137A, and yellow-green, RHS 147A.

*Mature color, abaxial surface.*—Nearest to yellow-green, in between RHS 146A and 146B.

*Venation.*—Vein pattern — Pinnate. Vein color, adaxial surface — Yellow-green, nearest to RHS N144C. Vein color, abaxial surface — Yellow-green, nearest to RHS N144C.

*Petiole.*—Length — 21.3 cm, including the geniculum. Width — 0.4 cm. Texture and luster, both surfaces — Smooth, glabrous and glossy. Color, adaxial surface — Yellow-green, nearest to RHS 144A. Color, abaxial surface — Yellow-green, nearest to RHS 144A. Strength — Very strong. Geniculum — Length — Approximately 2.2 cm. Width — Approximately 0.5 cm. Color — Yellow-green, nearest to RHS 145A. Petiole wings — Length — Approximately 2.8 cm. Width — Approximately 0.5 cm. Color — Green, nearest to RHS 143C. Stipule — Occurrence — A dry stipule is present at the base of each petiole. Shape — Narrow oblong. Apex — Acute. Base — Broad cuneate. Dimensions — 4.9 cm long and 0.8 cm wide. Texture and luster, both surfaces — Smooth, glabrous, and matte. Color, both surfaces — Greyed-orange, in between RHS 165B and 166B.

Inflorescence:

*Type.*—Consisting of a spathe and spadix.

*Arrangement.*—Inflorescences are carried slightly in between and above the leaf plane.

*Quantity per clump.*—2.

*Quantity per plant.*—6.

*Natural flowering season.*—Winter into spring.

*Height of spathe.*—6.3 cm.

*Time to flowering.*—13 weeks.

*Fragrance.*—Non fragrant.

*Self-cleaning or persistent.*—Persistent.

*Flower longevity.*—Flowers stay in good condition for approximately 4 weeks.

*Peduncle.*—Cross-section — Elliptical. Attitude — Approximately 20 degrees to the lateral branch axis. Length — Approximately 35.0 cm. Diameter — Approximately 0.45 cm. Texture and luster, both surfaces — Smooth, glabrous, and moderately glossy. Color — Yellow-green, nearest to RHS 146D, and suffused with greyed-orange, RHS 165C. Strength — Strong.

Spathe:

*Aspect.*—Horizontal; apex pointed downward at approximately 60 degrees from horizontal.

*Length.*—Approximately 12.6 cm.

*Width.*—Approximately 12.6 cm.

*Shape.*—Cordate.

*Aspect.*—Slightly convex.

*Margin.*—Entire; lightly undulated.

*Apex.*—Apiculate to short apiculate.

*Base.*—Unequal cordate.

*Texture and luster, upper surface.*—Smooth, glabrous, and very glossy.

*Texture and luster, lower surface.*—Smooth, glabrous, and very glossy.

*Color.*—Upper surface, when opening — Red, nearest to RHS 45B. Lower surface, when opening — Red, nearest to RHS 47B. Upper surface, when fully opened — Red, nearest to RHS 45B. Lower surface, when fully opened — Red, nearest to in between RHS 46B and 47B. Venation on the upper surface, when fully opened — Red, nearest to RHS 45B. Venation on the lower surface, when fully opened — Red, nearest to RHS 46A. Upper surface when fading — Red, nearest to RHS 45A. Lower surface when fading — Red, nearest to RHS 47C, and suffused with yellow-green, nearest to in between RHS 146C and 146D.

Spadix:

*Aspect.*—Approximately 70 degrees to the spathe.

*Shape.*—Cylindrical.

*Apex.*—Obtuse.

*Base.*—Obtuse.

*Length.*—Approximately 4.6 cm.

*Width.*—Approximately 1.0 cm.

*Texture and luster.*—Smooth, glabrous, and matte.

*Color.*—When opening — White, nearest to RHS NN155A; apex is yellow, RHS 13A. When fully opened — Nearest to a combination of white, RHS NN155A and yellow at the apex, nearest to in between RHS 18C and 18D. When fading — Yellow-green, nearest to RHS 146D.

*Quantity of flowers per spadix.*—Approximately 200.

*Spadix flower arrangement.*—Spirally placed on spadix.

*Spadix flower shape.*—Flattened; rotate.

*Spadix flower diameter.*—Approximately 2 mm.

*Spadix flower depth.*—Approximately 0.8 mm.

Reproductive organs:

*Androecium.*—Stamen quantity — 4. Filament — Dimensions — Approximately 0.75 mm long and approximately 0.25 mm in diameter. Color — A combination of light yellow to white; R.H.S. color designations cannot be determined due to the minute nature of the filament. Anther — Anther shape — Narrow, oblong with a longitudinal slit forming two halves. Anther size — 0.5 mm long and 0.25 mm in diameter. Anther color — Yellow, nearest to RHS 11D. Pollen — Amount of pollen — Scarce. Pollen color — Yellow, nearest to RHS 11D.

*Gynoecium.*—Pistil quantity — One. Length — 0.5 mm. Stigma — Shape — Club-shaped. Dimensions — Approximately 0.3 mm across and 0.15 mm tall. Color — Yellow-orange, nearest to RHS 22A. Style — Length — 0.35 mm. Color — Yellow-orange, nearest to in between RHS 18C and 18D. Ovary — Color — Yellow-orange, nearest to in between RHS 18C and 18D.

Seed and fruit: Seed production has not been observed.

COMPARISONS WITH THE PARENT

Plants of the new cultivar 'ARAANTRED1' differ from the seed parent, *Anthurium* 'K37', in the following characteristics described in Table 1 below.

TABLE 1

| Characteristic | 'ARAANTRED1' | 'K37' |
|---|---|---|
| Leaf size. | Smaller than 'K37'. | Larger than 'ARAANTRED1'. |
| General coloration of mature foliage. | Darker green. | Lighter green. |
| Spathe, aspect. | Near flat. | Convex. |
| Spadix dimensions. | Shorter, with a larger diameter. | Longer with a smaller diameter. |

Plants of the new cultivar 'ARAANTRED1' may be distinguished from the pollen parent, 'K38', by the following combination of characteristics described in Table 2 below.

TABLE 2

| Characteristic | 'ARAANTRED1' | 'K38' |
|---|---|---|
| Leaf size. | Smaller leaves. | Larger leaves. |
| General coloration of mature foliage. | Darker green. | Lighter green. |

TABLE 2-continued

| Characteristic | 'ARAANTRED1' | 'K38' |
|---|---|---|
| Leaf shape. | Narrower than 'K38'. | Wider than 'ARAANTRED1'. |
| Spadix dimensions. | Shorter, with a larger diameter. | Longer with a smaller diameter. |

COMPARISONS WITH THE MOST SIMILAR VARIETY OF COMMON KNOWLEDGE

Plants of the new cultivar 'ARAANTRED1' differ from the commercial variety, *Anthurium* 'ANTHCANYH' (not patented in the United States; Community Plant Variety Rights grant number 29823; Japanese Plant Breeder's Rights grant number 22592), in the following characteristics described in Table 3 below.

TABLE 3

| Characteristic | 'ARAANTRED1' | 'ANTHCANYH' |
|---|---|---|
| Leaf apex. | Apiculate. | Bluntly apiculate. |
| General coloration of mature foliage. | Darker green. | Lighter green. |
| General coloration of the spathe. | More vibrant red. | Less vibrant red. |
| Spathe luster. | Very glossy. | Less glossy. |
| Spadix apex. | Obtuse. | Narrowly obtuse. |

That which is claimed is:

1. A new and distinct variety of *Anthurium* plant named 'ARAANTRED1', substantially as described and illustrated herein.

* * * * *